(12) United States Patent
Bennett et al.

(10) Patent No.: US 9,289,188 B2
(45) Date of Patent: Mar. 22, 2016

(54) ULTRASONIC TRANSDUCER

(71) Applicant: LipoSonix, Inc., Hayward, CA (US)

(72) Inventors: Frederick Jay Bennett, Bellevue, WA (US); John P. Collins, Woodinville, WA (US); Blake W. Little, Bothell, WA (US)

(73) Assignee: LIPOSONIX, INC., Hayward, CA (US)

( * ) Notice: Subject to any disclaimer, the term of this patent is extended or adjusted under 35 U.S.C. 154(b) by 293 days.

(21) Appl. No.: 13/692,338

(22) Filed: Dec. 3, 2012

(65) Prior Publication Data

US 2014/0155747 A1 Jun. 5, 2014

(51) Int. Cl.
| | |
|---|---|
| *A61B 8/00* | (2006.01) |
| *A61B 8/14* | (2006.01) |
| *A61N 7/02* | (2006.01) |
| *H04R 31/00* | (2006.01) |
| *B06B 1/06* | (2006.01) |
| *A61N 7/00* | (2006.01) |

(52) U.S. Cl.
CPC ................ *A61B 8/4494* (2013.01); *A61B 8/14* (2013.01); *A61B 8/4444* (2013.01); *A61B 8/54* (2013.01); *A61N 7/02* (2013.01); *B06B 1/0625* (2013.01); *H04R 31/00* (2013.01); *A61B 8/4405* (2013.01); *A61N 2007/0052* (2013.01); *A61N 2007/0082* (2013.01); *Y10T 29/49005* (2015.01)

(58) Field of Classification Search
CPC ............................ B06B 1/0625; B06B 1/0651
See application file for complete search history.

(56) References Cited

U.S. PATENT DOCUMENTS

| | | | |
|---|---|---|---|
| 4,155,259 A | | 5/1979 | Engeler |
| 4,398,325 A | * | 8/1983 | Piaget et al. ................. 29/25.35 |
| 4,518,889 A | | 5/1985 | 'T Hoen |
| 4,641,660 A | | 2/1987 | Bele |
| 4,801,835 A | * | 1/1989 | Nakaya et al. ................ 310/358 |
| 5,044,462 A | * | 9/1991 | Maki, Jr. ........................ 181/103 |
| 5,485,843 A | | 1/1996 | Greenstein et al. |
| 5,520,188 A | | 5/1996 | Hennige et al. |
| 6,865,140 B2 | | 3/2005 | Thomenius et al. |
| 6,868,594 B2 | | 3/2005 | Gururaja |
| 7,053,530 B2 | * | 5/2006 | Baumgartner et al. ....... 310/334 |
| 7,621,028 B2 | | 11/2009 | Gelly et al. |
| 7,622,853 B2 | * | 11/2009 | Rehrig et al. .................. 600/459 |

(Continued)

FOREIGN PATENT DOCUMENTS

WO WO2009083896 * 7/2009 ............. G01K 11/00

*Primary Examiner* — Long V Le
*Assistant Examiner* — Kevin Pontius
(74) *Attorney, Agent, or Firm* — Thompson Hine LLP; Toan Vo

(57) ABSTRACT

An ultrasound transducer and methods of fabricating and using the ultrasound transducer. The ultrasound transducer includes a composite layer having a first surface and comprising a plurality of piezoelectric elements separated by isolating material filled kerfs. The composite layer is configured so that the first surface includes an exposed face of each element of the plurality of piezoelectric elements. The transducer further includes a plurality of electrodes defined on the first surface, the electrodes having boundaries configured so that none of the exposed faces are in contact with more than one of the plurality of electrodes. The electrodes may be defined in a conductive layer deposited on the first surface of the composite body by forming a channel in the conductive layer that is aligned vertically with the dielectric kerfs. The transducer may be used to scan a treatment region with both HIFU and imaging ultrasound signals.

22 Claims, 6 Drawing Sheets

(56) References Cited

U.S. PATENT DOCUMENTS

| | | |
|---|---|---|
| 7,841,984 B2 | 11/2010 | Cribbs et al. |
| 7,857,773 B2 | 12/2010 | Desilets et al. |
| 7,993,289 B2 | 8/2011 | Quistgaard et al. |
| 8,008,842 B2 | 8/2011 | Jiang et al. |
| 8,343,051 B2 | 1/2013 | Desilets et al. |
| 2004/0217675 A1 | 11/2004 | Desilets et al. |
| 2005/0154314 A1 | 7/2005 | Quistgaard |
| 2006/0122509 A1 | 6/2006 | Desilets |
| 2007/0167813 A1* | 7/2007 | Lee et al. ............ 600/459 |
| 2007/0232913 A1* | 10/2007 | Lau et al. ............ 600/439 |
| 2008/0125658 A1* | 5/2008 | Lee et al. ............ 600/459 |
| 2009/0171252 A1 | 7/2009 | Bockenstedt et al. |
| 2010/0042019 A1 | 2/2010 | Desilets et al. |
| 2010/0049098 A1 | 2/2010 | Shalgi et al. |
| 2010/0240998 A1* | 9/2010 | Calisti et al. ............ 600/446 |
| 2010/0249669 A1 | 9/2010 | Ulric et al. |
| 2011/0178443 A1 | 7/2011 | Desilets |

\* cited by examiner

ULTRASONIC TRANSDUCER

TECHNICAL FIELD

The present invention relates generally to medical ultrasound systems and, more particularly, to multi-element ultrasound transducers having reduced cross-talk between the elements, and methods of using and fabricating the same.

BACKGROUND

Ultrasound is commonly known for its uses in non-therapeutic medical procedures, such as tissue imaging for diagnostic purposes. High Intensity Focused Ultrasound (HIFU) is a medical procedure that uses highly focused ultrasound energy to heat and destroy diseased or other unwanted tissue. HIFU systems thereby use ultrasound energy to provide therapeutic benefits in a non-invasive manner. In order to achieve the desired physical effects in the targeted tissue, HIFU involves much higher acoustic intensity levels than diagnostic ultrasound. These high acoustic energy levels are typically obtained by using a transducer that focuses the ultrasound into a focal zone below the skin of the patient being treated. HIFU transducers are therefore typically formed with a spherical shape to provide a nominal focal distance near the middle of a desired range of focal depths. HIFU transducers may also include an array of elements so that the focal distance may be electrically adjusted relative to the nominal focal distance. To treat a desired region of the patient that is larger than the focal zone, the transducer may be moved relative to the region being treated, and/or the focal distance of the transducer adjusted. In this way, the focal zone may be moved to different positions within the desired treatment region until a sufficient dose of HIFU has been delivered.

Thus, there is a need for improved devices, systems, and methods for delivering ultrasound energy to selected regions within a patient using transducers having electrically adjustable focal distances.

BRIEF SUMMARY

In one embodiment, an apparatus is provided that includes a composite layer having a first surface and a second surface generally parallel to the first surface. The composite layer includes an isolating material and a plurality of piezoelectric elements, each of the piezoelectric elements being suspended in the isolating material and having a face exposed on the first surface of the composite layer. The apparatus further includes a plurality of electrodes on the first surface of the composite layer. Each electrode is directly coupled to at least one of the faces and is configured so that the face of each of the piezoelectric elements is directly coupled to no more than one electrode of the plurality of electrodes.

In another embodiment, a method is provided for fabricating an ultrasound transducer. The method includes providing a substrate that includes a piezoelectric layer, and forming a plurality of kerfs in the substrate to define a plurality of piezoelectric elements that are separated by the kerfs. The kerfs are filled with an isolating material to form a composite layer having a first surface. The composite layer includes the plurality of piezoelectric elements, each of the piezoelectric elements being separated from adjacent piezoelectric elements by the isolating material. The method further includes forming a plurality of electrodes on the first surface of the composite layer, the electrodes being defined so that each piezoelectric element is directly coupled to no more than one electrode of the plurality of electrodes.

In another embodiment, a method is provided for treating a patient with ultrasound. The method includes generating a High Intensity Focused Ultrasound (HIFU) focal zone with a transducer, and scanning the HIFU focal zone across a treatment region to provide a therapeutic dose of ultrasound energy to a portion of the treatment region. The method further includes generating an ultrasound imaging beam with the transducer, and scanning the ultrasound imaging beam across the treatment region. Echoes of the ultrasound imaging beam are received with the transducer, and an image of the portion of the treatment region is generated from the received echoes.

BRIEF DESCRIPTION OF THE SEVERAL VIEWS OF THE DRAWINGS

The accompanying drawings, which are incorporated in and constitute a part of this specification, illustrate various embodiments of the invention and, together with the general description of the invention given above and the detailed description of the embodiments given below, serve to explain the embodiments of the invention.

DETAILED DESCRIPTION

Embodiments of the invention are generally related to multi-element transducers for High Intensity Focused Ultrasound (HIFU) systems. In an embodiment of the invention, the transducer includes a layer of composite material that includes a plurality of piezoelectric pillars or elements separated by an isolating material, such as an epoxy. The composite layer may be formed by cutting kerfs in a solid layer of piezoelectric material and/or a multilayer material including piezoelectric and de-matching layers, and depositing the isolating material in the kerfs. The transducer may also include a plurality of annular electrodes on a first surface of the composite layer. The electrodes may be defined in a layer of conductive material on the first surface of the composite layer by a plurality of channels that separate the electrodes. To improve isolation between the annular electrodes, the channels are configured so that the electrodes do not share piezoelectric elements. This may be achieved by vertically aligning the channels separating the electrodes with the isolating material filled kerfs. By configuring the channels to coincide with the isolating material filled kerfs, electro-mechanical cross-talk between annular array elements of the transducer may be reduced without introducing deleterious mixed-mode vibrations.

The reduced crosstalk between elements that results from this improved isolation may allow the individual annular elements to be driven with signals having larger relative delays. This increase in the range of relative delays may in turn increase the adjustable depth of focus for the transducer, which may improve ultrasound imaging detail. The improved depth of focus may be particularly advantageous in planar transducer arrays, which are typically limited by their minimum electrically adjustable focal distance. Because ultrasound imaging requires good depth of focus, the improved depth of focus and larger bandwidths provided by embodiments of the invention may allow ultrasonic images to be generated during HIFU treatment using a shared transducer.

Figure 1:
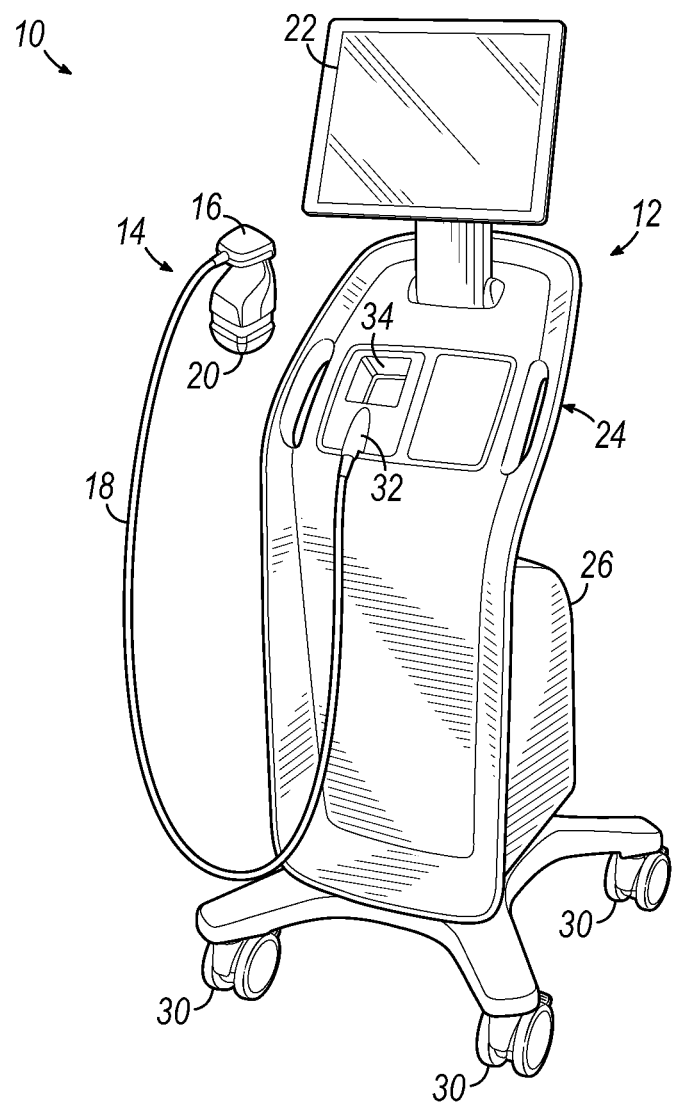
FIG. 1 is a diagrammatic view of a High Intensity Focused Ultrasound (HIFU) treatment and imaging system including a console, treatment head, and a Replaceable Treatment Cartridge (RTC).

FIG. 1 illustrates an exemplary HIFU system 10 that includes a console 12 and a treatment head 14. The treatment head 14 includes a handpiece 16 that couples to the console 12 via a cable 18, and a Replaceable Treatment Cartridge (RTC) 20 that is removably coupled to the treatment head 14. The console 12 may include a display 22 and a base unit 24 comprising a housing 26 that provides space for system circuitry and that serves as a platform for the system 10. The display 22 may include a touch screen device that provides a user interface 28 which allows an operator to control the system 10. A plurality of wheels 30 may be coupled to the base unit 24 so that the system can be rolled between areas where patients are treated. A connection point 32 having one or more signal ports and that is configured to accept a connectorized end of cable 18 may be provided in the base unit 24 to facilitate coupling different treatment heads 14 to the console 12. The base unit 24 may also include one or more receptacles 34 that provide a convenient storage place for system components and accessories, such as the handpiece 16.

Figure 2:
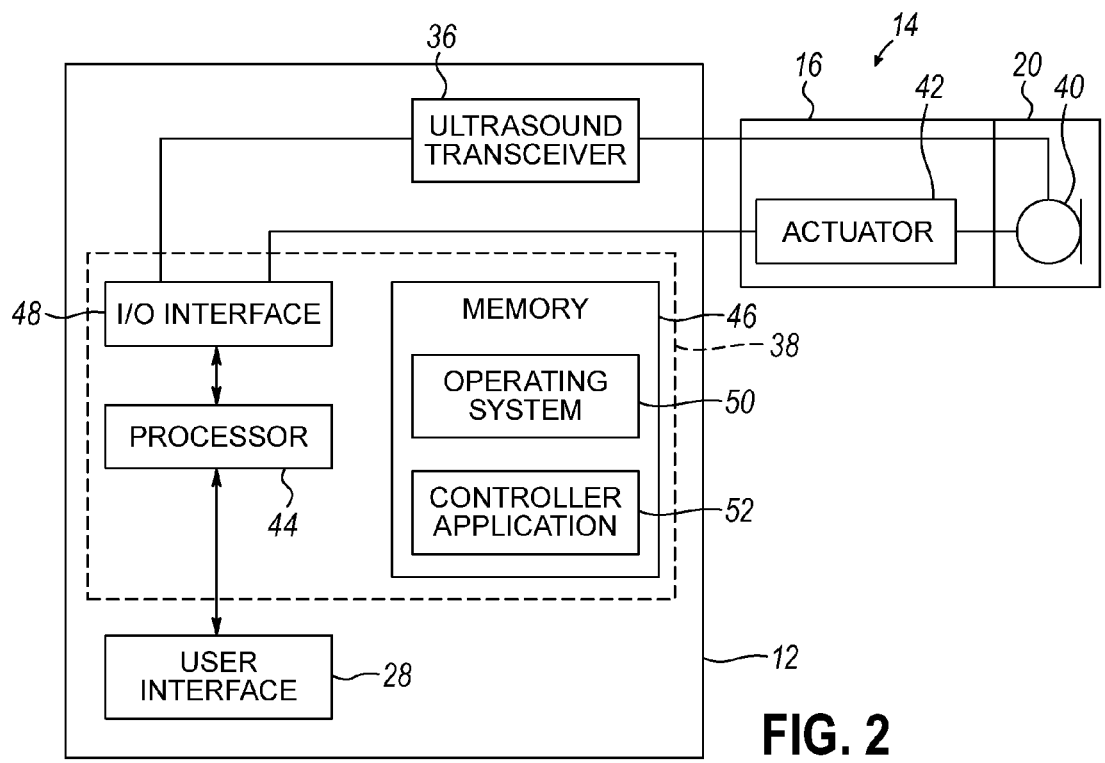
FIG. 2 is a schematic of the HIFU system of FIG. 1 showing additional details of the system.

FIG. 2 is a block diagram of the HIFU system 10 illustrating details of the treatment head 14, as well as an ultrasound transceiver 36 and system controller 38, which may be located in the console 12. The RTC 20 of treatment head 14 may include an ultrasound transducer 40 that is mechanically coupled to an actuator 42 in the handpiece 16. The actuator 42 may be operatively coupled to the controller 38 and configured to selectively position the transducer 40 within the RTC 20 in response to signals from the controller 38. The ultrasound transceiver 36 may be operatively coupled to the transducer 40, and is configured to transmit ultrasound signals to, and receive ultrasound signals from the transducer 40. The transceiver 36 may also be configured to process ultrasound signals through one or more beam-forming circuits to electrically adjust the focal distance of the transducer 40.

The controller 38 includes a processor 44, a memory 46, and an input/output (I/O) interface 48. The user interface 28 may be operatively coupled to the processor 44 of controller 38 in a known manner to allow a system operator to interact with the controller 38. The processor 44 may include one or more devices selected from microprocessors, micro-controllers, digital signal processors, microcomputers, central processing units, field programmable gate arrays, programmable logic devices, state machines, logic circuits, analog circuits, digital circuits, or any other devices that manipulate signals (analog or digital) based on operational instructions that are stored in the memory 46. Memory 46 may be a single memory device or a plurality of memory devices including but not limited to read-only memory (ROM), random access memory (RAM), volatile memory, non-volatile memory, static random access memory (SRAM), dynamic random access memory (DRAM), flash memory, cache memory, or any other device capable of storing digital information. Memory 46 may also include a mass storage device (not shown) such as a hard drive, optical drive, tape drive, non-volatile solid state device or any other device capable of storing digital information.

Processor 44 may operate under the control of an operating system 50 that resides in memory 46. The operating system 50 may manage controller resources so that computer program code embodied as one or more computer software applications, such as a controller application 52 residing in memory 46 may have instructions executed by the processor 44. In an alternative embodiment, the processor 44 may execute the applications 52 directly, in which case the operating system 50 may be omitted. The I/O interface 48 operatively couples the processor 44 to other components of the HIFU system 10, including the ultrasound transceiver 36 and actuator 42. The I/O interface 48 may include signal processing circuits that condition incoming and outgoing signals so that the signals are compatible with both the processor 44 and the components to which the processor 44 is coupled. To this end, the I/O interface 48 may include analog to digital (A/D) and/or digital to analog (D/A) converters, voltage level and/or frequency shifting circuits, optical isolation and/or driver circuits, and/or any other analog or digital circuitry suitable for coupling the processor 44 to the other components of the HIFU system 10.

Figure 3:
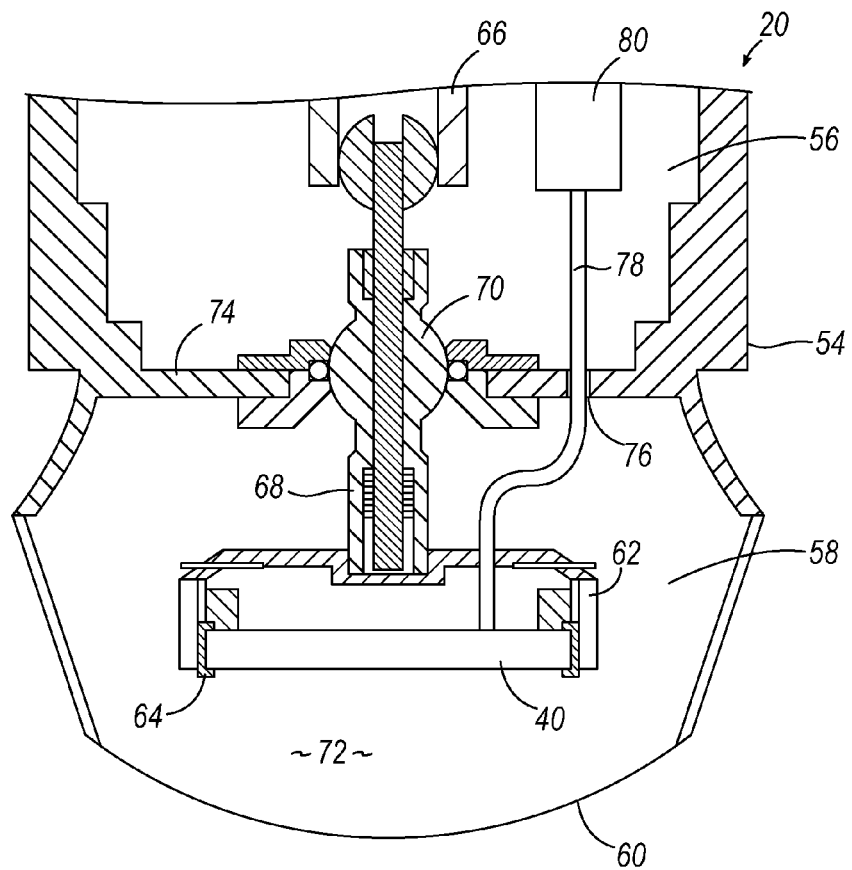
FIG. 3 is a cross-sectional view of an embodiment of the RTC of FIG. 1 showing details of an ultrasound transducer assembly.

Referring now to FIG. 3, the RTC 20 may include a housing 54 having an upper chamber 56 and a lower chamber 58. The lower chamber 58 may include an acoustically transparent window 60 through which acoustic energy may be coupled to a patient, and an ultrasound transducer assembly 62 that includes the transducer 40. The transducer 40 may be coupled to the transducer assembly 62 via a mounting flange 64 that is bonded or otherwise attached to the perimeter of the transducer 40. The mounting flange 64 may provide a resilient surface for coupling the transducer 40 to the transducer assembly 62. The transducer assembly 62 may serve as a heat sink for the transducer 40 as well as coupling the transducer 40 to a mechanical interface 66 via a control arm 68. The transducer 40 may thereby be moved or pivoted within the lower chamber 58 with the control arm 68 by applying force to the mechanical interface 66. In alternative embodiments, the transducer assembly 62 may be fixedly coupled to the RTC 20, in which case the control arm 68 may be omitted, or may be coupled to the RTC 20 by another type of mechanism, such as an x-y positioner. Persons having ordinary skill in the art will therefore understand that embodiments of the invention are not limited to an RTC 20 that locates the transducer assembly 62 with a control arm 68.

In embodiments including the control arm 68, the control arm 68 may be located by a ball mount 70 so that the transducer assembly 62 can be oriented within the lower chamber 58 via the mechanical interface 66. The lower chamber 58 may be filled with a coupling medium 72, such as degassed water. The coupling medium 72 may acoustically couple the transducer 40 to the window 60 as well as conduct heat away from the transducer assembly 62. A partition 74 separates the upper chamber 56 from the lower chamber 58 so that the coupling medium 72 is confined to the lower chamber 58. The partition 74 may include a sealed aperture 76 that provides a pass-through for a transducer coupling cable 78 that electrically couples the transducer 40 to the transceiver 36 via an electrical interface 80.

Figure 4A:
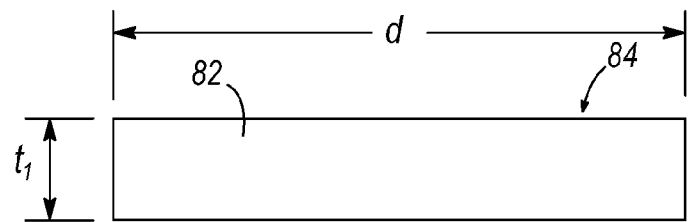
FIGS. 4A-4E are cross-sectional views that illustrate a process for forming a piezoelectric composite layer.
Figure 4B:
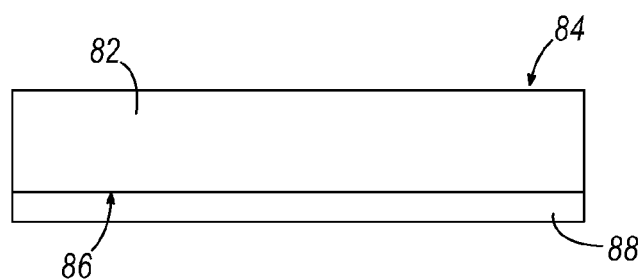

Referring now to FIGS. 4A and 4B, the transducer 40 may be fabricated from a solid piece of piezoelectric material 82 having a desired transducer shape, such as a disk having a top surface 84 and a bottom surface 86. For example, the piezoelectric material 82 may be a disk of Lead Zirconate Titanate (PZT-8) or equivalent having a diameter d of between 15 and 16 mm and a thickness $t_1$ of between 0.4 and 0.5 mm in the case of a transducer for use at a frequency of 3.75 MHz. For a transducer intended to operate at a lower frequency, such as 2.00 MHz, the dimensions of the piezoelectric material may be larger. For example, the diameter d may be about 38 mm and the thickness $t_1$ between 1.1 and 1.2 mm for a transducer intended to operate at 2.00 MHz. As illustrated in FIG. 4B, to provide support to the piezoelectric material 82 during fabrication of the transducer 40, the bottom surface 86 of piezoelectric material 82 may be bonded to a support layer 88, such as a polyester or thermoplastic film carrier.

Figure 4C:
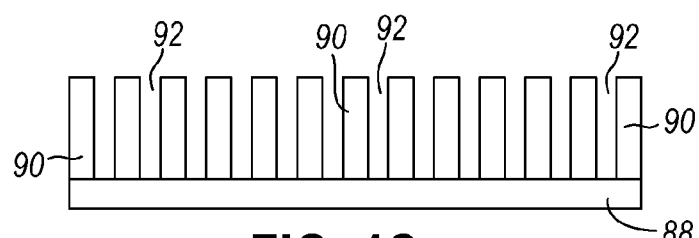

Referring now to FIG. 4C, the support layer 88 may maintain the positions of a plurality of piezoelectric elements 90 defined from the piezoelectric material 82 by kerfs 92. The kerfs 92 may be cut to a depth that reaches the bottom surface 86 of piezoelectric material 82 so that the resulting piezoelectric elements 90 are fully separated, as shown. The kerfs 92 may also stop just short of the bottom surface 86, in which case the elements 90 may be connected by a thin layer of the remaining piezoelectric material 82. Typically, the kerfs 92 are formed by dicing the piezoelectric material 82 with a saw, although the kerfs 92 may be formed using any suitable method, such as patterning a masking layer using photolithography followed by an etching step. Typical dimensions of the kerfs 92 for a transducer 40 intended to operate at 3.75 MHz may be a width of between 0.025 mm and 0.060 mm, and a pitch of about 0.25 mm. Typical dimensions for the kerfs may vary based on the intended frequency of operation. For example, a 2.00 MHz transducer 40 may have kerfs 92 with a width of between 0.045 and 0.056 mm and a pitch of between 0.36 and 0.55 mm. In an embodiment of the invention intended to operate with a center frequency of 3.75 MHz, 51 kerfs 92 may be cut in each of two horizontal directions to define 2500 individual piezoelectric elements 90.

Figure 4D:
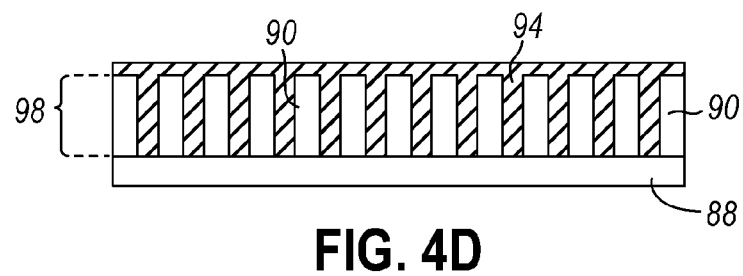

Referring now to FIG. 4D, after the kerfs 92 are formed, they may be filled with an isolating material 94 to form dielectric regions between the piezoelectric elements 90. Suitable isolating materials may include an epoxy, polymer, resin, or any other material that can flow into the kerfs 92 while in a fluid state and be cured to a solid state that provides sufficient mechanical strength to hold the piezoelectric elements 90 in place. For example, the isolating material 94 may be a heat cured epoxy having a shore hardness ≥80. To provide a clean surface and promote adhesion, the diced piezoelectric material 82 may be plasma etched prior to deposition of the isolating material 94. The isolating material 94 may also be sufficiently compliant at ultrasound frequencies so as to provide acoustic isolation between the piezoelectric elements 90. A composite body or layer 98 may thereby be formed that includes piezoelectric elements 90 that are electrically and acoustically isolated from each other by the isolating material 94. The isolating material 94 provides support and maintains the piezoelectric elements 90 in a fixed position relative to one another. The resulting composite layer 98 thereby comprises the individual piezoelectric elements 90 and the isolating material 94 used to suspend and hold the elements 90 in place.

Figure 4E:
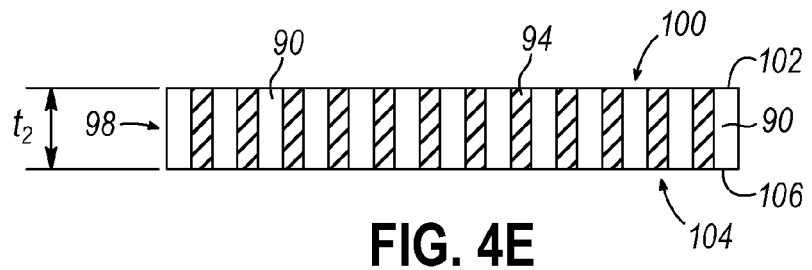

Referring now to FIG. 4E, after the isolating material 94 has cured, a top surface 100 of composite layer 98 may be formed by grinding or lapping to remove excess isolating material 94. Lapping the top surface 100 of composite layer 98 may also planarized the top surface 100 and expose top faces 102 of the piezoelectric elements 90. Similarly, grinding or lapping may be used to remove the support layer 88. This lapping may also form a planarized bottom surface 104 of composite layer 98 that likewise includes exposed bottom faces 106 of the piezoelectric elements 90. Lapping the bottom surface 104 may also be used to adjust the final thickness $t_2$ of the composite layer 98, and to isolate the piezoelectric elements 90 in cases where the kerfs 92 are not cut completely through the piezoelectric material 82. For example, in an alternative embodiment of the invention, depth of the kerfs 92 may such that a sufficient amount of the piezoelectric material 82 remains to hold the piezoelectric elements 90 in place until the isolating material 94 is cured. In this alternative embodiment, the support layer 88 may be omitted. In another alternative embodiment, a layer of de-matching material (not shown) may be bonded to the bottom surface 86 of piezoelectric material 82 prior to processing. In this embodiment, the kerfs 92 may be cut completely through the de-matching layer, or may be cut only part way through or into the de-matching layer to form compound piezoelectric elements 90 including a section comprised of the piezoelectric material 82 and a section comprised of the de-matching material.

In any case, a typical composite layer 98 for a 2.00 MHz transducer may have a final thickness $t_2$ of between 0.83 and 0.87 mm, while the thickness of the composite layer 98 for a 3.75 MHz transducer may be between 0.4 and 0.45 mm. The resulting composite layer 98 includes the plurality of piezoelectric elements 90 suspended in the isolating material 94. The piezoelectric elements 90 are oriented so that the top face 102 of piezoelectric element 90 is exposed and generally level with the top surface 100 of composite layer 98, and the bottom face 106 of piezoelectric element 90 is exposed and generally level with the bottom surface 104 of composite layer 98. In an embodiment of the invention, the piezoelectric elements 90 may be in the form of vertical pillars having a rectangular cross-section.

Figure 5A:
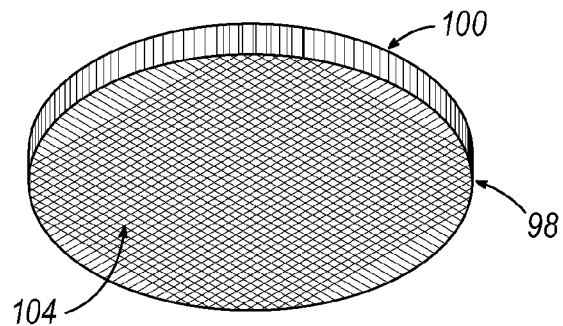
FIGS. 5A-5C are perspective views that illustrate a process for fabricating a transducer from the composite layer of FIG. 4E.

Referring now to FIG. 5A, the resulting composite layer 98 may be in the form flat disc comprised of a plurality of columnar piezoelectric elements 90 having rectangular horizontal cross sections and held together by the isolating material 94. Although the composite layer 98 is shown in the illustrated embodiments as a flat disk, in alternative embodiments, the composite layer 98 may have other shapes, such as a square.

Figure 5B:
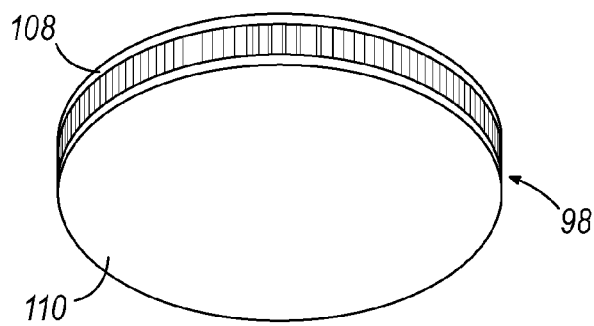

As shown in FIG. 5B, a first conductive layer 108 may be deposited on the top surface 100 of composite layer 98. A second conductive layer 110 may be deposited on the bottom surface 104 of composite layer 98 so that electrical fields can be applied vertically across the piezoelectric elements 90. The conductive layers 108, 110 may be deposited by any suitable method, such as chemical deposition, sputtering, evaporation, and/or plating one or more layers of a suitable metal, such as copper, gold, or aluminum onto the respective surface 100, 104 of composite layer 98. For example, the conductive layers 108, 110 may be formed by sputtering 0.75 to 1.0 microns of gold over an adhesion seed layer, such as titanium. To provide a clean surface on which to deposit the metal, the composite layer 98 may be plasma etched prior to deposition of the conductive layers 108, 110. In an alternative embodiment, the entire outer surface of the composite layer 98 may be coated with a conductive layer in a single step. In this alternative embodiment, the first and second conductive layers 108, 110 may be electrically coupled by a circumferential layer (not shown) of the sputtered gold that is deposited on the vertical side surface of the composite layer 98.

Figure 5C:
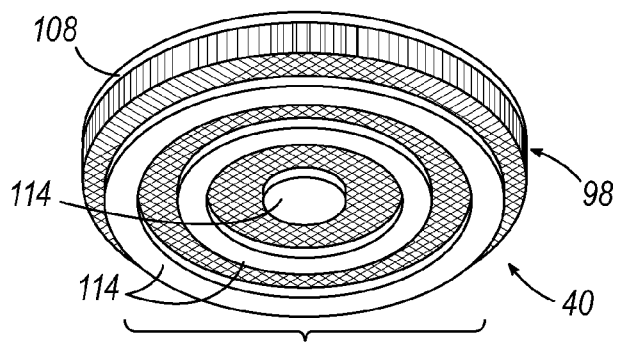

Referring now to FIG. 5C, a radiating region 112 of the transducer 40 may be formed by a plurality of electrodes 114 defined in the second conductive layer 110. Each of the electrodes 114 may be electrically coupled to the bottom faces 106 of one or more elements of the plurality of piezoelectric elements 90 so that voltages coupled to the electrodes 114 produce electric fields across the corresponding piezoelectric elements 90 of transducer 40.

Figure 6:
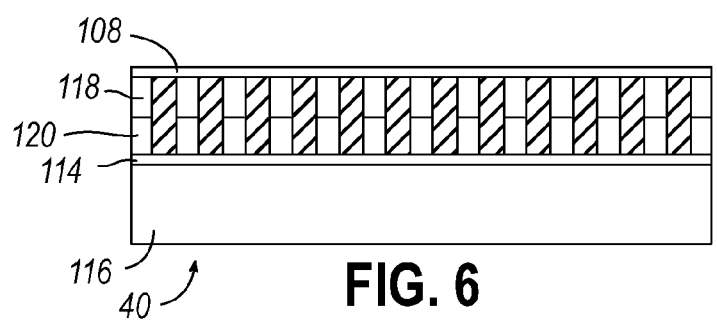
FIG. 6 is a cross-sectional view of a transducer including a matching layer and compound piezoelectric elements having active and de-matching sections.

Referring now to FIG. 6, to improve the efficiency of the transducer 40, an acoustic matching layer 116 may be coupled to the bottom surface 104 of composite layer 98. The acoustic impedance Z of a substance is defined by $Z=\rho \times C$, where C is the sonic velocity in the material and p is the density of the material. When an acoustic wave encounters a boundary between materials having different acoustic impedances, part of the acoustic wave is reflected back toward the source of the acoustic energy. The acoustic impedance and layer thickness of the matching layer 116 may be chosen to produce destructive interference in waves reflected from the interfaces between the coupling medium 72, the piezoelectric elements 90, and the matching layer 116. This destructive interference may reduce or cancel the reflected waves so that a larger fraction of the acoustic energy generated by the transducer 40 is coupled into the coupling medium 72. The acoustic matching layer 116 may thereby match the acoustic impedance of the piezoelectric elements 90 to the acoustic impedance of the coupling medium 72 and improve the efficiency of the transducer 40. The matching layer 116 may also increase the amount of acoustic energy that is coupled from the coupling medium 72 to the piezoelectric elements 90, which may increase the sensitivity of the transducer 40 when used for imaging applications. Although shown as a single layer in FIG. 6, the matching layer 116 may include a plurality of layers having various impedances and thicknesses to improve the impedance match over an operational frequency range of the transducer 40. For example, the matching layer 116 may include two or more layers of materials having various thicknesses and acoustic impedances to broaden the frequency range over which the acoustic impedance of the transducer 40 is matched to the coupling medium 72.

To further improve the efficiency of the transducer 40, the piezoelectric elements 90 may be compound elements comprising a de-matching section 118 and an active section 120. The de-matching section 118 may be comprised of the de-matching material, and the active section 120 may be comprised of the piezoelectric material 82. Compound piezoelectric elements 90 may be fabricated by substituting a disc comprising a first layer of piezoelectric material bonded to a second layer of de-matching material for the homogenous piezoelectric material 82 shown in FIG. 4A. Suitable de-matching materials may include tungsten, tungsten carbide, and molybdenum. The de-matching section 118 works on a similar principle as the matching layer 116, except that the acoustic impedance and layer thickness of the de-matching material is chosen to increase acoustic reflections at the interface between the de-matching section 118 and active section 120. The reflections may be increased by selecting a material with a high acoustic impedance, such as a material having an impedance >70 MRalyls. The de-matching materials may also exhibit good heat and electrical conductivity, which may allow transducers 40 having compound piezoelectric elements 90 to have improved cooling and electrical properties. The de-matching section 118 may thereby improve mechanical packaging and thermal management of the transducer 40 as compared to transducers lacking the de-matching section 118.

The introduction of the de-matching sections 118 to the piezoelectric elements 90 may also allow the piezoelectric elements 90 to resonate in a quarter wavelength mode instead of the half wavelength mode typical of transducers 40 having non-compound or homogeneous piezoelectric elements 90. That is, the thickness of the active section 120 of the compound piezoelectric element 90 may be about $\lambda/4$, or about half the $\lambda/2$ vertical dimension of homogeneous piezoelectric elements 90 operating in the same frequency range. The reduced vertical dimension of the piezoelectric section 120 of the compound piezoelectric element 90 may reduce the electrical impedance of the transducer 40 by about half, thereby reducing the voltages required to drive the transducer 40.

Figure 7:
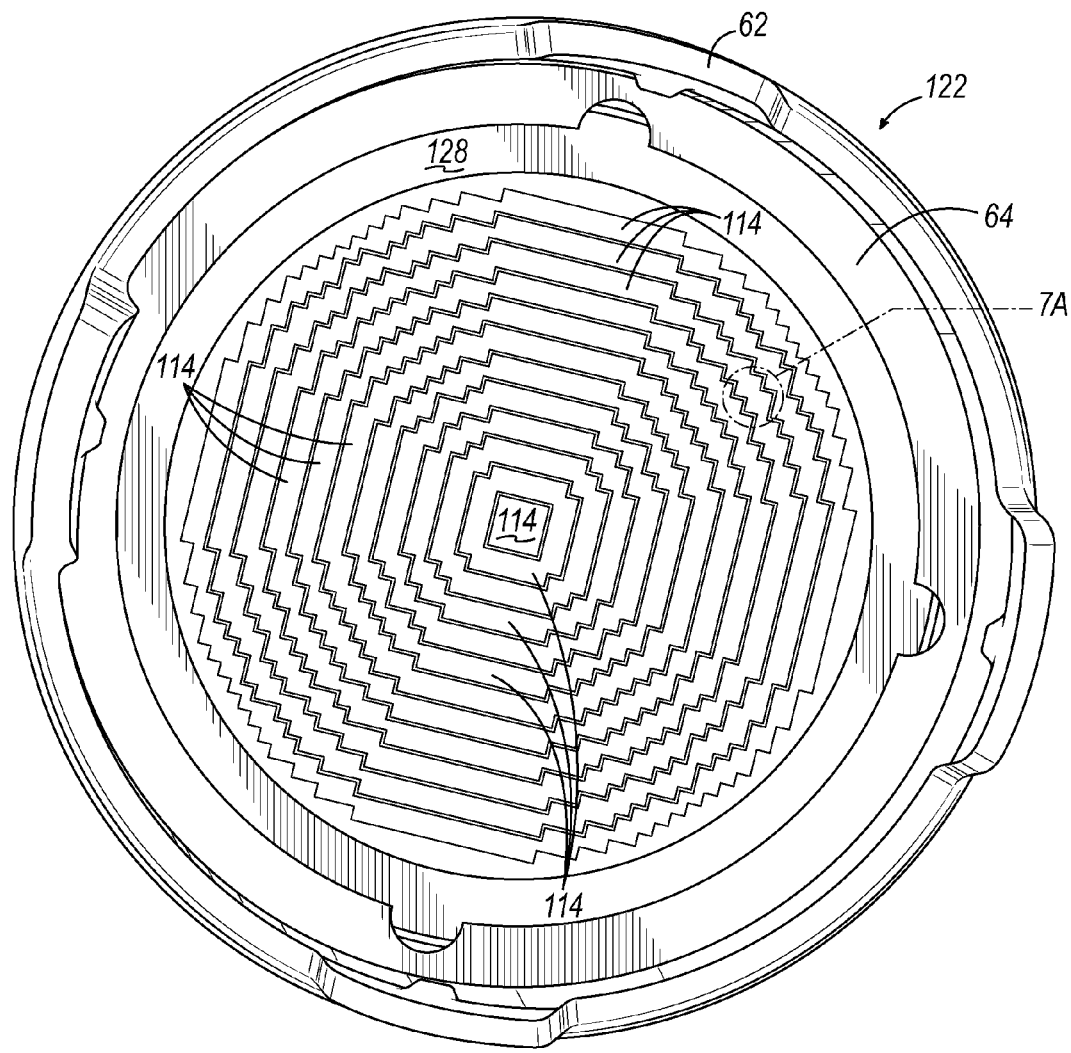
FIG. 7 is a top view of a transducer in accordance with an embodiment of the invention.
Figure 7A:
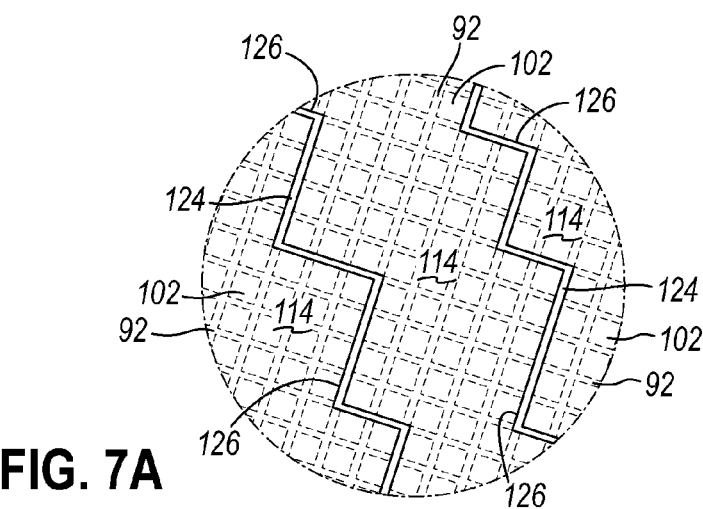
FIG. 7A is a close-up view of an area of the transducer in FIG. 7 showing additional details of the transducer.

Referring now to FIGS. 7 and 7A, a transducer 122 in accordance with an embodiment of the invention is presented. The electrodes 114 of transducer may be defined in the second conductive layer 110 by forming isolation channels 124 that define perimeters 126 of the electrodes 114. These isolation channels 124 may be formed electrically by scribing, mechanically by micro-machining (i.e., ultrasonic machining, water jet machining, laser etching, or combinations thereof), or using photolithography followed by chemical or plasma etching of the second conductive layer 110. For example, isolation channels 124 having a width of 0.06 mm may be laser scribed in the second conductive layer 110. The laser scribes may be aligned with the kerfs 92 so that the resulting isolation channels 124 are generally vertically aligned with the dielectric regions between the piezoelectric elements 90. After isolation, the electrodes 114 may exhibit a DC resistance ≥20 mega ohms.

The transducer 122 is shown mounted in the transducer assembly 62 according to an embodiment of the invention. The transducer 122 includes electrodes 114 configured in a generally concentric annular arrangement to define the acoustic radiating region 112 of the transducer 122. As shown in FIG. 7, the transducer 122 has 12 concentric annular electrodes 114 with a generally constant width or pitch, although other numbers of annular electrodes may be used. The diameter for the transducer 122 will typically depend on the intended operating frequency of the transducer 122 and the intended depth of treatment. For example, a transducer intended to operate at 3.75 MHz may have a diameter of between 15 and 16 mm and a composite body thickness of between 0.6 and 0.8 mm. In contrast, a transducer intended to operate at 2.00 MHz may have a diameter of about 38 mm and a composite body thickness of between 0.8 and 0.9 mm. The transducer 122 may also include peripheral ground ring 128 at the transducer's perimeter. The ground ring 128 may be formed from the same conductive layer 110 used to form the electrodes 114, and may be electrically coupled to the first conductive layer 108 by a circumferential conductive layer (not shown) deposited on the vertical sides of the composite layer 98 in essentially the same manner as the first and second conductive layers 108, 110.

The ground ring 128 may also be electrically coupled to the assembly 62 by the mounting flange 64. The ground ring 128 may thereby provide an area on the bottom surface 104 of composite layer 98 that is electrically coupled to the first conductive layer 108. The isolation channels 124 may be vertically aligned with the kerfs 92 so that none of the piezoelectric elements 90 have a bottom face 106 that is directly coupled to more than one annular electrode 114. As best shown in FIG. 7A, the resulting annular electrodes 114 are thereby directly coupled to the bottom faces 106 of an integral number of piezoelectric elements 90 to form a pixilated or discrete pattern of squares that approximates a circular ring. By ensuring that the individual piezoelectric elements 90 are not shared between annular electrodes 114, cross-talk and mixed mode vibration effects related to mechanical isolation may be reduced as compared to conventional transducer arrays lacking this feature.

Aligning the isolation channels 124 so that the channels 124 are coincident with the kerfs 92 of the composite layer 98 may improve containment of the electrical fields generated between each of the annular electrodes 114 and the first conductive layer 108. The electric field associated with each annular electrode 114 may thereby be isolated from neighboring annular electrodes 114. This electric field containment and resulting neighbor isolation may be a result of the difference in dielectric constants between the piezoelectric elements 90 (which typically have a dielectric constant greater than 500) and the isolating material 94 (which typically has a dielectric value of about 3).

Cross-talk measurements on prototype transducers using the above design techniques have shown a reduction in cross-talk of approximately 18 dB as compared to conventional adjustable focus annular array transducers. Annular arrays formed using the aforementioned method have also proven easier to fabricate because the annular array elements may be defined using a constant pitch scheme as opposed to an equal area scheme. The constant pitch scheme allows for the laser scribing pattern to be easily defined, and is compatible with the dicing pattern of the piezoelectric composite material. The improved cross-talk performance provided by transducers configured in accordance with embodiments of the invention offer the potential for both improved ultrasonic imaging and HIFU focal zone control.

Due to the high power levels that must be delivered to the treatment region, HIFU treatment has the potential to damage regions of the body between where the ultrasound enters the patient and the region to be treated. By coupling the ultrasound energy to the patient through a relatively large surface area and focusing the energy into a concentrated region or focal zone below the skin, HIFU transducers prevent undesired damage to the skin and other intervening layers of the patient's body. In this way, therapeutic intensity levels may be achieved in the treatment region without damaging intervening tissue between the ultrasound entrance location and the region to be treated.

In order to treat a volume of tissue within the patient, the focal zone may be moved in three dimensions so that therapeutic doses of ultrasound are delivered to the desired treatment region. To control the depth of the focal zone, the HIFU system 10 may electrically adjust the focal distance of the transducer 122 by processing signals provided to the electrodes 114 through a beam-former in the ultrasound transceiver 36. The beam-former may delay signals provided to the inner electrodes 114 relative to the outer electrodes 114 so that the resulting ultrasound waveform generated by the transducer 122 is concave. By controlling the relative phase and intensity of the HIFU signal provided to each ring of the annular array, the acoustic energy produced by the transducer 122 may be caused to converge at varying distances from the transducer 122. The transducer 122 can thereby be driven in a way that produces a shorter focal distance to treat regions closer to the surface of the patient, and a longer focal distance to treat regions deeper within the patient.

To image a region of the patient, an imaging beam is typically generated by transmitting one or more short (i.e., broadband) bursts of ultrasound. As the ultrasound burst travels through the patient, reflections caused by features in the region being imaged scatter the ultrasound, some of which may be scattered back towards the transducer 122. After the burst is transmitted, the electrodes 114 are coupled to a receive beam-former in the ultrasound transceiver 36. The receive beam-former may adjust the focal distance of the transducer 122 to receive back scattered echoes from a desired depth. The transducer 122 may generate electrical signals in response receiving the backscattered echoes, and these received echo signals are coupled to the transceiver 36. In the transceiver 36, the received echo signals are processed by the receive beam-former, which may perform a dynamic delay-and-sum operation to electrically adjust the focal distance of transducer 122 dynamically based on the amount of time since the imaging burst was transmitted. Early in the receive cycle, when the ultrasonic wave has propagated a short distance into the patient, the focusing delay profile of the receive beam-former may be configured to focus the transducer 122 at a shallow depth corresponding to the depth of the ultrasonic wave. As time passes, echoes from deeper within the treatment region are expected, and the delay profile of the receive beam-former may be adjusted accordingly so that the transducer 122 has a longer electrical focal distance. The receive beam-former thereby focuses the transducer 122 at whatever depth from which echoes are being received so that the received beam pattern is as narrow as possible given the transducer characteristics. The intensity of the received echoes thereby provide a one-dimensional density profile of echoes verses depth along this beam. To provide a 2-dimensional image of the treatment region, this beam may be swept through the treatment region. Persons having ordinary skill in the art will understand that other methods of generating the 2-dimensional image may also be used. Embodiments of the invention are therefore not limited to a particular method of generating the 2-dimensional image.

If signals provided to one electrode of a transducer are undesirably coupled to other elements of the array, the resulting cross-talk between array electrodes may reduce the ability of the transducer to form a well defined focal zone, create excessive heating in the transducer or electrical drive circuitry, and may also result in radial and lateral acoustic modes that cause ultrasound energy to be radiated in undesirable directions. For these reasons, high crosstalk levels may reduce the maximum delays that can be applied by the beam-formers, reducing the range over which the focal distances of a conventional transducer may be adjusted. Cross-talk may be particularly limiting when performing ultrasound imaging due to the higher bandwidths typically required, with the higher frequency content having higher crosstalk levels. A poorly defined focal zone may also contribute to blurring of the ultrasound images. Thus, to produce an HIFU transducer that can also be used for ultrasound imaging, the crosstalk between array elements of the transducer must be controlled.

Figure 8:
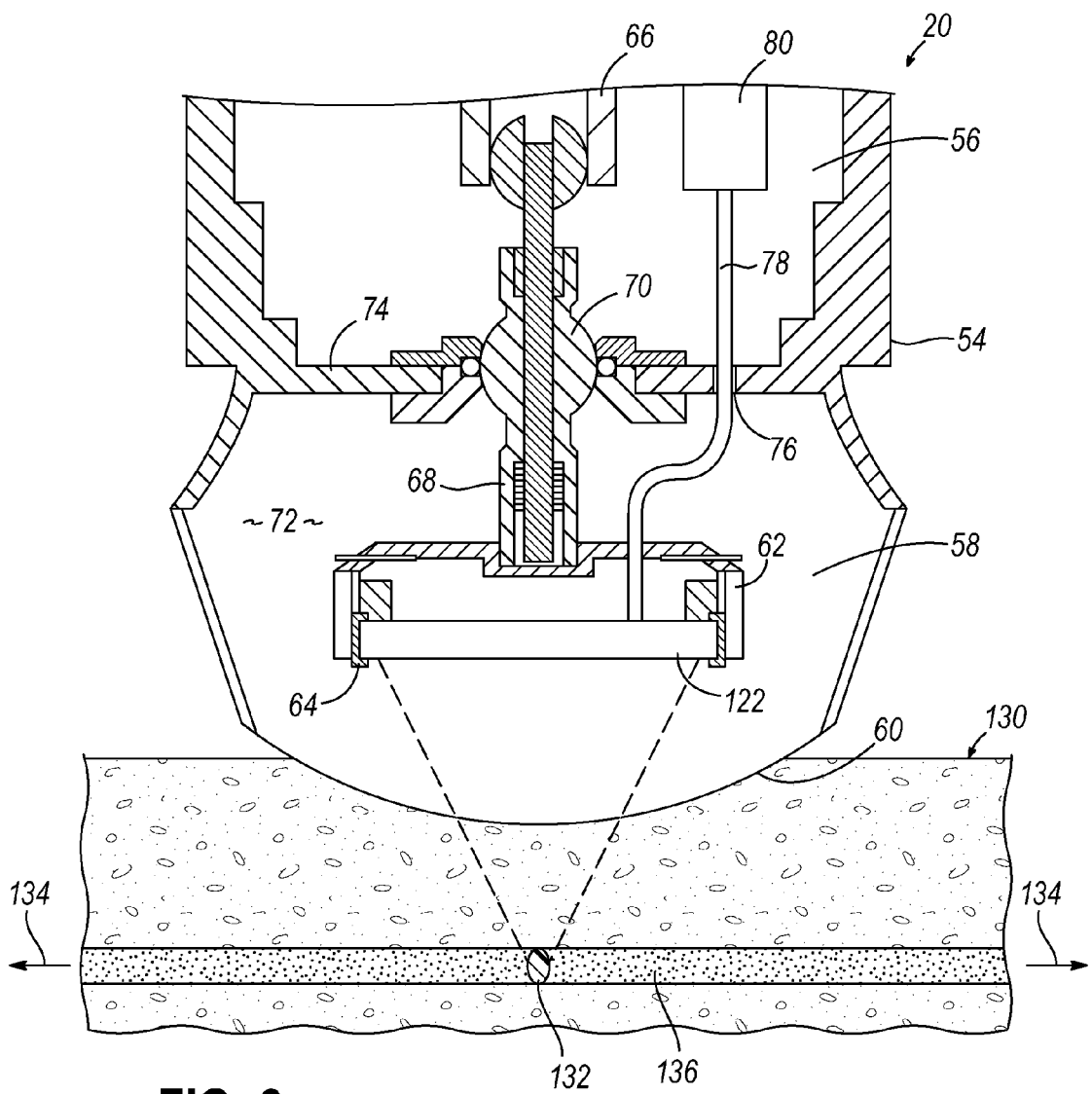
FIG. 8 is a cross-sectional view of a region of a patient to be treated with HIFU.

FIG. 8 is a cross-sectional view of a treatment region 130 of a patient with the RTC 20 placed against the patient's body surface or skin. In operation, the transducer 122 may be excited with ultrasound signals so that a focal zone 132 of concentrated ultrasound energy is formed in the treatment region 130. The transducer assembly 62 may be moved via the control arm 68 so that the focal zone 132 is swept along a scan line 134 in a generally linear direction through the treatment region 130. By providing sufficient ultrasound energy to the focal zone 132, the heat produced may cause necrosis of tissue in the treatment region 130 so that a continuous lesion 136 is formed along the scan line 134. The dose of HIFU delivered to the focal zone 132, and thus the heat provided to the scan line 134, may be controlled by varying the intensity of the ultrasound, the scan velocity, or both the intensity and velocity. By moving or pivoting the transducer assembly 62 back and forth in a controlled pattern, multiple lesions 136 may be created so that a selected region of the treatment area is exposed to a controlled dose of ultrasound energy. A therapeutic dose of ultrasound energy may be characterized by a rise in temperature at or near the focal zone 132 that causes collagen denaturing and/or necrosis. For example, a temperature above 37° C. may produce collagen denaturing over a sufficient amount of time. More typically, higher temperatures are used to speed the process. For example, a temperature of 46° C. may produce therapeutic effects within several minutes, while a temperature of 56° C. may produce therapeutic effects within a few seconds. An energy flux provided by the RTC 20 during HIFU therapy to achieve these temperatures will typically range from at least 35 J/cm$^2$ to as high as 460 J/cm$^2$ at the surface of the of the patient.

Figure 9:
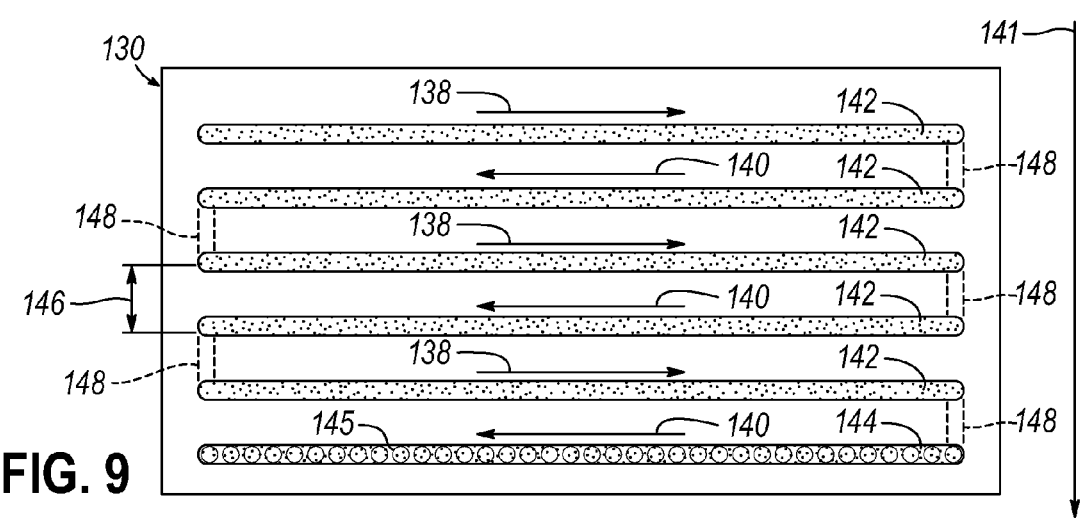
FIG. 9 is a top view of the treatment region of FIG. 8 showing a pattern of scan lines.

FIG. 9 is a top view of the treatment region 130 shown in FIG. 8 that illustrates how selected areas of the treatment region 130 may be exposed to therapeutic levels of ultrasound energy by moving the transducer assembly 62 in a raster pattern. This movement may cause the transducer assembly 62 to sweep the focal zone 132 back and forth across the treatment region 130 so that a selected volume of the treatment region 130 is exposed to HIFU. To provide ultrasound images of the treatment area 130 in real time during HIFU treatment, the transducer 122 may be excited with a mixture of HIFU and imaging signals while the transducer assembly 62 is alternately scanned in a first direction (as indicated by arrows 138), and a second direction (as indicated by arrows 140). In an embodiment of the invention, HIFU and imaging scan lines may be generated while the handpiece 16 is moved along a line of movement (indicated by arrow 141) generally orthogonal to the first and second scan line directions 138, 140. The HIFU treatment and imaging scan lines may be interleaved, and may have equal or unequal numbers. That is, the HIFU treatment and imaging scan lines may be generated alternately, and/or there may be multiple scan lines of one type between each scan line of the other type. Moreover, the ratio of HIFU to imaging scan lines may be adjusted based on the speed the handpiece 16 is moved along the line of movement 141. For example, as shown in the illustrated embodiment, the system may be configured to generate five HIFU scan lines 142 followed by a "quiet" period to let the ultrasound energy dissipate before generating an imaging scan line 144. The rate and positioning of the imaging scan lines 144 may be selected so that the imaging scan lines 144 provide a continuous image as the treatment region 130 is scanned and/or the handpiece 16 is moved along the line of movement 141.

The resulting scan pattern may comprise an interleaved pattern of HIFU treatment scan lines 142 and ultrasonic imaging scan lines 144 having various numbers and combinations of each scan line type. The HIFU scan line 142 may be exposed to a continuous level of HIFU energy (as shown), or may be provided with bursts of HIFU energy. The imaging scan line 144 may consist of a plurality of closely spaced imaging bursts 145, which may allow a two-dimensional image of the treatment region to be generated. In an embodiment of the invention, the timing parameters for generating imaging scan lines 144 may be configured to generate 128 imaging scan lines 144 along the length of the movement line 141 (e.g., over the area being imaged and/or treated). These imaging scan lines 144 may be spaced equally along the line of movement 141 so that the resulting image presents an undistorted view of the region being treated. Based on how fast the handpiece 16 is moving and/or the treatment region 130 is being scanned, the requirement for equally spaced imaging lines 144 may determine how many HIFU scan lines 142 can be scanned between the imaging scan lines 144.

Although shown as separate scan lines in FIG. 9 for the purposes of clarity, line spacing 146 may be adjusted so that HIFU scan lines 142 and imaging scan lines 144 partially or fully overlap, and to control the distance between HIFU scan lines 142. For example, parallel HIFU scan lines 142 may be placed close together or in an overlapping arrangement so that thermal energy from one HIFU scan line 142 adds to the amount of thermal energy provided to treated tissue by the adjacent HIFU scan line 142. The horizontal scan lines 142, 144 may be connected with vertical transit lines 148 during which the transducer 122 will typically be inactive. The system may also utilize movement of the handpiece 16 along the line of movement 141 to space the HIFU and imaging scan lines 142, 144. The vertical transit lines 148 may also be subjected to ultrasound energy if the transducer 122 is active while moving vertically. Multiple treatments may also be provided to the same treatment area 130 by repeating the raster pattern, or with patterns having different crossing or overlapping of scan lines so that a desired dose of HIFU is provided to the treatment region 130. Methods of scanning a treatment region are described in more detail in U.S. Publication No. 2010/0249669 filed on Mar. 4, 2010 and entitled "Ultrasonic Treatment of Adipose Tissue at Multiple Depths", the disclosure of which is incorporated herein by reference in its entirety. In any case, persons having ordinary skill in the art will understand that there are numerous scanning patterns that may be used to cover the treatment region 130, and embodiments of the invention are not limited to a particular scanning pattern.

The ability to image the patient with the transducer 122 may allow the HIFU system 10 to provide the system operator with ultrasonic images of the treatment region 130 during treatment. These real-time images may improve the operator's ability to control or adjust HIFU treatment as the treatment is being administered. This instant visual feedback may improve the accuracy with which HIFU treatment is provided to the patient, as well as reduce the time required to prepare and treat the patient. For example, using conventional methods, the treating physician may use ultrasound imaging prior to treatment with HIFU to identify a volume of tissue to be treated. The corresponding surface area of the patient adjacent to the volume to be treated may then be marked with contour lines to provide a guide during subsequent HIFU treatment. By providing the operator with real-time images during HIFU treatment, this laborious pre-treatment process may be omitted. The ability to guide the RTC 20 across the patient based on real time ultrasound images may therefore eliminate the need for optical mouse tracking or to mark the skin of the patient with contour lines prior to treatment.

It will be understood that when an element is described as being "connected" or "coupled" to or with another element, it can be directly connected or coupled to the other element or, instead, one or more intervening elements may be present. In contrast, when an element is described as being "directly connected" or "directly coupled" to another element, there are no intervening elements present. When an element is described as being "indirectly connected" or "indirectly coupled" to another element, there is at least one intervening element present.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "in response to" means "in reaction to" and/or "after" a first event. Thus, a second event occurring "in response to" a first event may occur immediately after the first event, or may include a time lag that occurs between the first event and the second event. In addition, the second event may be caused by the first event, or may merely occur after the first event without any causal connection.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. An apparatus comprising:
   a composite layer having a first surface and a second surface generally parallel to the first surface, the composite layer including a plurality of piezoelectric elements, a plurality of kerfs, and an isolating material in the kerfs, and each piezoelectric element having a first face exposed at the first surface of the composite layer; and
   a conductive layer including a first annular electrode on the first surface of the composite layer, a second annular electrode on the first surface of the composite layer, and an isolation channel between the first annular electrode and the second annular electrode, the isolation channel vertically aligned with the kerfs to separate the first annular electrode from the second annular electrode, the first face of each of the piezoelectric elements directly coupled to either the first annular electrode or the second annular electrode, and the isolation channel entirely coinciding with the kerfs.

2. The apparatus of claim 1 wherein the first annular electrode and the second annular electrode are concentrically arranged.

3. The apparatus of claim 1 wherein each piezoelectric element of the plurality of piezoelectric elements includes:
   a piezoelectric section including the first face and a second face opposite the first face; and
   a de-matching section coupled to the second face of the piezoelectric section, the de-matching section having an acoustical impedance that causes acoustic energy incident on the de-matching section from the piezoelectric section to be reflected back toward the piezoelectric section.

4. The apparatus of claim 3 further comprising:
   a heat sink thermally coupled to the de-matching section of each piezoelectric section.

5. The apparatus of claim 3 further comprising:
   an ultrasound transceiver electrically coupled with the de-matching section of each piezoelectric section.

6. The apparatus of claim 3 wherein each piezoelectric section has a thickness that is less than one half of a wavelength of a center frequency of an operational frequency range.

7. The apparatus of claim 6 wherein the thickness of each piezoelectric section is one fourth of the wavelength of the center frequency.

8. The apparatus of claim 1 wherein the first surface of the composite layer is planar.

9. The apparatus of claim 1 further comprising:
   a treatment head including an actuator coupled to the composite layer and a chamber that encloses the composite layer;
   a transceiver operatively coupled to the first annular electrode and the second annular electrode; and
   a controller operatively coupled to the actuator and the transceiver, the controller configured to selectively activate the transceiver to:
     transmit first electrical signals to the first annular electrode and the second annular electrode that generate a High Intensity Focused Ultrasound (HIFU) focal zone;
     transmit second electrical signals to the first annular electrode and the second annular electrode that generate an ultrasound imaging beam; and
     receive third electrical signals from the first annular electrode and the second annular electrode corresponding to echoes of the ultrasound imaging beam, the controller being further configured to generate an ultrasound image from the third electrical signals received by the transceiver.

10. The apparatus of claim 9, wherein the controller is further configured to operate the actuator so that the HIFU focal zone is scanned along a first plurality of scan lines in a treatment region, and the ultrasound imaging beam is scanned along a second plurality of scan lines in the treatment region.

11. The apparatus of claim 10 wherein the controller is configured to operate the actuator so that the first plurality of scan lines are interleaved with the second plurality of scan lines.

12. A method of fabricating an ultrasound transducer, the method comprising:
   providing a substrate that includes a piezoelectric layer;
   forming a plurality of kerfs in the substrate to define a plurality of piezoelectric elements that are separated by the kerfs;
   filling the kerfs with an isolating material to form a composite layer having a first surface and a second surface generally parallel to the first surface, the composite layer including the isolating material and the plurality of piezoelectric elements, and each of the piezoelectric elements having a first face exposed at the first surface of the composite layer;
   depositing a conductive layer on the first surface of the composite layer; and
   forming an isolation channel in the conductive layer between a first annular electrode and a second annular electrode on the first surface, each of the first and second annular electrodes comprised of material from the conductive layer, the isolation channel vertically aligned with the kerfs, the first face of each of the piezoelectric elements directly coupled to either the first annular electrode or the second annular electrode, and the isolation channel entirely coinciding with the kerfs.

13. The method of claim 12 wherein forming the plurality of kerfs in the substrate includes:
   bonding a support layer to a second surface of the substrate;

curing the isolating material so that the isolating material changes from a fluid state into a solid state;

in response to the isolating material being cured, removing the support layer from the second surface; and lapping the second surface of the composite layer to obtain a desired thickness of the composite layer.

14. The method of claim 12 further comprising:

lapping the first surface of the composite layer to expose the first face of each piezoelectric element.

15. The method of claim 12 wherein providing the substrate comprises:

bonding a layer of de-matching material to the piezoelectric layer.

16. A method of treating a patient with ultrasound, the method comprising:

generating a High Intensity Focused Ultrasound (HIFU) focal zone with a transducer including a plurality of piezoelectric elements, a plurality of kerfs separating the piezoelectric elements, an isolating material in the kerfs, and a conductive layer including an isolation channel vertically aligned with the kerfs, the isolation channel located between a first annular electrode and a second annular electrode, each of the first and second annular electrodes directly coupled to the first face of at least one of the piezoelectric elements and aligned with the kerfs, the first face of each of the piezoelectric elements directly coupled to either the first annular electrode or the second annular electrode, and the isolation channel entirely coinciding with the kerfs;

commencing a treatment by scanning the HIFU focal zone across a treatment region to provide a therapeutic dose of ultrasound energy to a portion of the treatment region;

generating an ultrasound imaging beam with the transducer during the treatment;

scanning the ultrasound imaging beam across the treatment region during the treatment;

receiving echoes of the ultrasound imaging beam with the transducer during the treatment; and generating an image of the portion of the treatment region from the received echoes during the treatment, wherein the vertical alignment of the isolation channel with the kerfs reduces cross-talk between the first annular electrode and the second annular electrode during the treatment.

17. The method of claim 16 wherein:

scanning the HIFU focal zone across the treatment region includes scanning the HIFU focal zone along a first plurality of scan lines in the treatment region, and scanning the ultrasound imaging beam across the treatment region includes scanning the ultrasound imaging beam along a second plurality of scan lines in the treatment region.

18. The method of claim 17 wherein scanning the ultrasound imaging beam along the second plurality of scan lines in the treatment region includes interleaving the second plurality of scan lines with the first plurality of scan lines.

19. The method of claim 16 wherein generating the HIFU focal zone comprises:

generating at least one ultrasound burst having a first duration.

20. The method of claim 19 wherein generating the ultrasound imaging beam comprises:

generating a plurality of ultrasound bursts each having a second duration less than the first duration.

21. The method of claim 16 further comprising:

adjusting, during the treatment, at least one of a power level of the HIFU focal zone, a scan speed of the HIFU focal zone, and a position of the HIFU focal zone within the treatment region based on the image generated from the received echoes.

22. The method of claim 16 wherein:

generating the ultrasound imaging beam with the transducer includes generating a burst of ultrasound energy; and generating the image of the portion of the treatment region from the received echoes includes electrically adjusting, during the treatment, a focal distance of the transducer based on an amount of time since the burst of ultrasound energy so that the focal distance corresponds to a depth of the treatment region from which an echo of the burst is expected.

* * * * *